US009937119B2

(12) United States Patent
Mendoza et al.

(10) Patent No.: US 9,937,119 B2
(45) Date of Patent: Apr. 10, 2018

(54) COSMETIC COMPOSITIONS

(71) Applicant: MARY KAY INC., Dallas, TX (US)

(72) Inventors: Ricky Mendoza, Dallas, TX (US); Barbara Durkee, Dallas, TX (US); Greg Norman, Dallas, TX (US); Geetha Kalahasti, Dallas, TX (US)

(73) Assignee: Mary Kay Inc., Addison, TX (US)

( * ) Notice: Subject to any disclaimer, the term of this patent is extended or adjusted under 35 U.S.C. 154(b) by 479 days.

(21) Appl. No.: 14/527,435

(22) Filed: Oct. 29, 2014

(65) Prior Publication Data

US 2015/0118176 A1 Apr. 30, 2015

Related U.S. Application Data

(60) Provisional application No. 61/896,975, filed on Oct. 29, 2013.

(51) Int. Cl.

| | | |
|---|---|---|
| *A61K 8/81* | (2006.01) | |
| *A61Q 19/10* | (2006.01) | |
| *A61Q 19/08* | (2006.01) | |
| *A61K 8/41* | (2006.01) | |
| *A61K 8/34* | (2006.01) | |
| *A61K 8/44* | (2006.01) | |
| *A61Q 19/00* | (2006.01) | |
| *A61K 8/92* | (2006.01) | |

(52) U.S. Cl.
CPC ............ *A61K 8/8152* (2013.01); *A61K 8/345* (2013.01); *A61K 8/41* (2013.01); *A61K 8/44* (2013.01); *A61K 8/922* (2013.01); *A61Q 19/00* (2013.01); *A61Q 19/08* (2013.01); *A61Q 19/10* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 2,798,053 A | 7/1957 | Brown et al. .................... 521/38 | |
| 3,755,560 A | 8/1973 | Dickert et al. ............. 511/772.6 | |
| 4,421,769 A | 12/1983 | Dixon et al. .................. 514/772 | |
| 4,509,949 A | 4/1985 | Huang et al. ...................... 8/558 | |
| 4,599,379 A | 7/1986 | Flesher et al. ................. 524/801 | |
| 4,628,078 A | 12/1986 | Glover et al. ............. 526/303.1 | |
| 4,835,206 A | 5/1989 | Farrar et al. .................. 524/457 | |
| 4,849,484 A | 7/1989 | Heard ........................... 525/221 | |
| 5,011,681 A | 4/1991 | Ciotti et al. ................... 510/136 | |
| 5,087,445 A | 2/1992 | Haffey et al. .................... 424/59 | |
| 5,100,660 A | 3/1992 | Hawe et al. ................. 424/78.35 | |
| 5,576,354 A | 11/1996 | Deflandre et al. ............. 514/685 | |
| 5,587,150 A | 12/1996 | Deflandre et al. .............. 424/59 | |
| 6,673,374 B2 * | 1/2004 | Murad ..................... A61K 8/22 424/616 | |
| 7,014,842 B2 | 3/2006 | Dueva-Koganov et al. ... 424/59 | |
| 2004/0109905 A1 | 6/2004 | Bagchi .......................... 424/732 | |
| 2005/0163880 A1 | 7/2005 | Pusateri et al. ............... 424/777 | |
| 2008/0051312 A1 * | 2/2008 | Lestage ................. A61K 8/046 510/475 | |
| 2009/0017147 A1 * | 1/2009 | Lintner .................. A61K 8/975 424/780 | |
| 2009/0197976 A1 | 8/2009 | Schultz et al. ................ 514/785 | |
| 2010/0022585 A1 * | 1/2010 | deLong ................ C07D 217/02 514/312 | |
| 2010/0234474 A1 * | 9/2010 | Lou .......................... A61K 8/06 514/675 | |
| 2012/0058076 A1 * | 3/2012 | Widgerow ............. A61K 36/23 424/78.02 | |
| 2012/0288478 A1 | 11/2012 | Florence et al. ............. 424/93.1 | |
| 2013/0315846 A1 | 11/2013 | Collier et al. .................. 424/59 | |

FOREIGN PATENT DOCUMENTS

| | | |
|---|---|---|
| CN | 1097193541 | 3/1997 |
| CN | 1997194857 | 4/1997 |
| CN | 1999812492 | 6/1999 |
| CN | 2000805101 | 2/2000 |
| CN | 1867316 | 11/2006 |
| CN | 200908148755 | 12/2009 |
| CN | 201010122699 | 3/2010 |
| CN | 2001812593 | 7/2010 |
| CN | 201180032364 | 6/2011 |
| CN | 201210279945 | 8/2012 |
| CN | 201210280020 | 8/2012 |
| CN | 103037838 | 4/2013 |
| WO | WO 2010/124280 | 10/2010 |
| WO | WO2010124280 A2 * | 10/2010 |
| WO | WO 2011/103449 | 8/2011 |

OTHER PUBLICATIONS

PCT Search Report and Written Opinion issued in PCT/US2014/062932 dated Feb. 17, 2015.
Supplementary Search Report issued in Chinese Application No. 2014800336167, dated Jan. 12, 2018.
Office Action issued in Chinese Application No. 20148003361637, dated Jan. 23, 2018.

* cited by examiner

*Primary Examiner* — Robert A Wax
*Assistant Examiner* — Quanglong N Truong
(74) *Attorney, Agent, or Firm* — Norton Rose Fulbright US LLP

(57) ABSTRACT

Disclosed are compositions and methods for their use that can be used individually or in combination. The compositions have the ability to treat a wide range of skin and skin conditions, and particularly men's skin.

20 Claims, No Drawings

COSMETIC COMPOSITIONS

CROSS REFERENCE TO RELATED APPLICATIONS

This application claims the benefit of U.S. Provisional Application No. 61/896,975, filed Oct. 29, 2013. The contents of the referenced application are incorporated herein by reference.

BACKGROUND OF THE INVENTION

A. Field of the Invention

The present invention relates generally to various skin formulations that are structured in such a way to treat a wide range of conditions in male skin. The formulations can be used separately or in combination.

B. Description of Related Art

There are thousands of skin formulations available to consumers. In addition, the skin of men has different needs from the skin of women and, while women have a large selection of skincare products to choose from, the options available formulated specifically for men are much fewer. This leaves them with the choice of having to identify one of a large number of female-designed products or of selecting from a narrower range of products designed for male skin, which results in a confusing and exhaustive search for different products for different applications.

SUMMARY OF THE INVENTION

The various formulations discovered by the inventors can be used on all types of skin. In particular aspects, however, the formulations work particularly well on men's skin. Further, when the formulations are used in combination, additional benefits can be obtained. The formulations may be creams, and may be capable of moisturizing skin, treating the skin around the eyes, or cleansing the skin.

In one instance, there is disclosed a topical skin composition that is capable of moisturizing skin and treating the skin around the eyes comprising any one of, any combination of, or all of water, glycerin, butylene glycol, ethylene/acrylic acid copolymer, *Butyrospermum parkii* butter, disodium EDTA, and triethanolamine. The amounts of the ingredients within the composition can vary (e.g., amounts can be as low as 0.000001% to as high as 70% w/w or any range therein). In one instance, the composition includes 25% to 70% w/w of water, 1% to 10% w/w of glycerin, 0.5% to 6% w/w of butylene glycol, 0.5% to 3% w/w of ethylene/acrylic acid copolymer, 0.5% to 5% w/w of *Butyrospermum parkii* butter, 0.01% to 0.2% w/w of disodium EDTA, and 0.05% to 1% w/w of triethanolamine.

In another aspect, there is disclosed a topical skin composition that is formulated as a cream and has a sun protection factor of around 30 comprising any one of, any combination of, or all of oxybenzone, octisalate, octocrylene, homosalate, avobenzone, styrene/acrylates copolymer, water, glycerin, butylene glycol, ethylene/acrylic acid copolymer, *Butyrospermum parkii* butter, disodium EDTA, and triethanolamine. The composition can further include any one of, any combination of, or all of: glycereth-26, allantoin, xantham gum, panthenol, tocopherol acetate, sodium PCA, benzyl alcohol, PEG-100 stearate, lauramine oxide, C9-15 alkyl phosphate, polymethylsilsesquioxane, methyl trimethicone, acrylates/dimethicone copolymer, trisiloxane, cetearyl alcohol, C12-15 alkyl benzoate, phenethyl benzoate, polyester-7, ceteth-20 phosphate, neopentyl glycol diheptanoate, dimethicone, dipropylene glycol dibenzoate, dicetyl phosphate, caprylyl glycol, methyl trimethicone, methyldihydrojasmonate, hydroxyethyl acrylate/sodium acryloyldimethyl taurate copolymer, pentylene glycol, squalane, ethylene brassylate, ethyl linalool, PPG-15 stearyl ether benzoate, sorbic acid, polysorbate 60, isobutyl methyl tetrahydropyranol, trimethylbenzenepropanol, sorbitan isostearate, phenylisohexanol, ammonium hydroxide, glyceryl stearate, arachidyl alcohol, potassium cetyl phosphate, steareth-21, hydrogenated palm glycerides, behenyl alcohol, arachidyl glucoside, hydrogenated lecithin, benzyl alcohol, hydroxyethyl acrylate/sodium acryloydimethyl taurate copolymer, C9-15 alkyl phosphate, tocopheryl acetate, phenoxyethanol, ceteryl alcohol, trimethypentanediol/adipic acid/glycerin crosspolymer, isobutyl methyl tetrahydropryranol, adenosine, and sodium benzoate. The composition can further include *Opuntia tuna* fruit extract. The amounts of the ingredients within the composition can vary (e.g., amounts can be as low as 0.000001% to as high as 70% w/w or any range therein). In one instance, the composition includes 25% to 70% w/w of water, 1% to 10% w/w of glycerin, 0.5% to 6% w/w of butylene glycol, 0.5% to 3% w/w of ethylene/acrylic acid copolymer, 0.5% to 5% w/w of *Butyrospermum parkii* butter, 0.01% to 0.2% w/w of disodium EDTA, 0.05% to 1% w/w of triethanolamine, and 15% to 30% w/w of a combination of oxybenzone, octisalate, octocrylene, homosalate, avobenzone, and styrene/acrylates copolymer. In some embodiments, the compositions may comprise 0.0001% to 0.1% w/w of *Opuntia tuna* fruit extract. Also contemplated is a method of protecting skin from UV radiation comprising topically applying the composition to skin in need thereof, wherein topical application of said composition protects the skin from UV radiation.

In yet another aspect, there is disclosed a topical skin composition formulated as a cream capable of reducing the appearance of dark circles or puffy eyes comprising any one of, any combination of, or all of water, glycerin, butylene glycol, ethylene/acrylic acid copolymer, *Butyrospermum parkii* butter, disodium EDTA, and triethanolamine. The composition can further include any one of, any combination of, or all of phenoxyethanol, Carbopol Ultrez 10, cetearyl glucoside, chlorphenesin, adenosine, betaine, Hispagel 200 NS, cetearyl alcohol, ceteareth-20, C12-15 alcohols benzoate, hydrogenated polydecene, polyethylene, cetyl esters, behenyl alcohol, eldew PS-304, dipalmit hydroxyproline, dimethicone silicone, Glycacil 2000, and palmitoyl tetrapeptide-7. The composition can further include *Opuntia tuna* fruit extract. The amounts of the ingredients within the composition can vary (e.g., amounts can be as low as 0.000001% to as high as 70% w/w or any range therein). In one instance, the composition includes 25% to 70% w/w of water, 1% to 10% w/w of glycerin, 0.5% to 6% w/w of butylene glycol, 0.5% to 3% w/w of ethylene/acrylic acid copolymer, 0.5% to 5% w/w of *Butyrospermum parkii* butter, 0.01% to 0.2% w/w of disodium EDTA, 0.05% to 1% w/w of triethanolamine, 0.5% to 1.5% w/w of phenoxyethanol, 0.2% to 0.4% w/w of Carbopol Ultrez 10, 0.5% to 1.5% w/w of cetearyl glucoside, 0.2% to 0.3% w/w of chlorphenesin, 0.01% to 0.1% w/w of adenosine, 1.0% to 5.0% w/w of betaine, 2.0% to 3.0% w/w of Hispagel 200 NS, 0.25% to 1.5% w/w of cetearyl alcohol, 0.25% to 1.5% w/w of ceteareth-20, 2.0% to 4.0% w/w of C12-15 alcohols benzoate, 2.0% to 3.0% w/w of hydrogenated polydecene, 2.0% to 3.0% w/w of polyethylene, 1.0% to 1.5% w/w of cetyl esters, 1.0% to 1.5% w/w of behenyl alcohol, 0.25% to 1.0% w/w of eldew PS-304, 0.25% to 1.0% w/w of dipalmit hydroxyproline, 0.5% to 1.5% w/w of dimethicone silicone, 0.1% to 0.2% w/w of Glycacil 2000, and 1.0% to 3.0% w/w of palmitoyl tetrapeptide-7. In some embodiments, the compositions may comprise 0.01% to 0.1% w/w of *Opuntia tuna* fruit extract. Also contemplated is a method of reducing the appearance of dark circles or puffiness in the periorbital region of a person's face comprising topically applying the compositions to skin in need thereof, wherein topical application reduces the appearance of dark circles or puffiness in the periorbital region of a person's face.

In a further aspect, there is a disclosed a cleanser comprising any one of, a combination of, or all of water, glycerin, triethanolamine, phenoxyethanol, disodium EDTA, hydroxypropyl cyclodextrin, iodopropynyl butylcarbamate, tea-lauryl sulfate, cocamidopropyl betaine, propylene glycol, sodium methyl cocoyl taurate, dimethicone, lauramine oxide, acrylates/C10-30 alkyl acrylate crosspolymer, sodium chloride, caprylyl glycol, C12-15 alkyl benzoate, benzyl alcohol, PEG-150 distearate, PPG-26-buteth-26, and PEG-40 hydrogenated castor oil. Further, additional ingredients can be added to obtain a desired tactile property and/or to obtain a particular skin benefit. The amounts of the ingredients within the composition can vary (e.g., amounts can be as low as 0.000001% to as high as 95% w/w or any range therein). In one instance, the composition includes 25% to 95% w/w of water, 1% to 10% w/w glycerin, 0.1% to 2% w/w triethanolamine, 0.1% to 2% w/w phenoxyethanol, 0.01% to 0.2% w/w disodium EDTA, 0.01% to 0.2% w/w hydroxypropyl cyclodextrin, 0.001% to 0.02% w/w iodopropynyl butylcarbamate, 5% to 10% w/w tea-lauryl sulfate, 1% to 3% w/w cocamidopropyl betaine, 1% to 3% w/w propylene glycol, 1% to 3% w/w sodium methyl cocoyl taurate, 1% to 3% w/w dimethicone, 0.1% to 3% w/w lauramine oxide, 0.1% to 3% w/w acrylates/C10-30 alkyl acrylate crosspolymer, 0.1% to 1% w/w sodium chloride, 0.1% to 1% w/w caprylyl glycol, 0.1% to 1% w/w C12-15 alkyl benzoate, 0.1% to 1% w/w benzyl alcohol, 0.1% to 1% w/w PEG-150 distearate, 0.1% to 1% w/w PPG-26-buteth-26, and 0.1% to 1% w/w PEG-40 hydrogenated castor oil.

Also, herein there is disclosed an aqueous gel that is capable of moisturizing skin. The aqueous gel can be a serum. The formulation can include one, a combination of, or all of water, glycerin, triethanolamine, phenoxyethanol, disodium EDTA, hydroxypropyl cyclodextrin, iodopropynyl butylcarbamate, butylene glycol, niacinamide, hydroxypropyl cyclodextrin, adenosine, acetyl dipeptide-1 cetyl ester, palmitoyl oligopeptide, palmitoyl tetrapeptide-7, acrylates/vinyl isodecanoate crosspolymer, and hydroxyethylcellulose. Further, additional ingredients can be added to obtain a desired tactile property and/or to obtain a particular skin benefit. The amounts of the ingredients within the composition can vary (e.g., amounts can be as low as 0.000001% to as high as 95% w/w or any range therein). In one instance, the composition includes 25% to 95% w/w of water, 1% to 10% w/w glycerin, 0.1% to 2% w/w triethanolamine, 0.1% to 2% w/w phenoxyethanol, 0.01% to 0.2% w/w disodium EDTA, 0.01% to 0.2% w/w hydroxypropyl cyclodextrin, 0.001% to 0.02% w/w iodopropynyl butylcarbamate, 5% to 10% w/w butylene glycol, 1% to 3% w/w niacinamide, 0.01% to 0.3% w/w hydroxypropyl cyclodextrin, 0.01% to 0.3% w/w adenosine, 0.001% to 0.1% w/w acetyl dipeptide-1 cetyl ester, 0.00001% to 0.001% w/w palmitoyl oligopeptide, 0.00001% to 0.001% w/w palmitoyl tetrapeptide-7, 0.1% to 3% w/w acrylates/vinyl isodecanoate crosspolymer, and 0.1% to 3% w/w hydroxyethylcellulose.

In yet another aspect of the invention there is disclosed a combination of ingredients that can work to simultaneously treat fine lines and wrinkles, inhibit or reduce skin pigmentation, and treat inflamed or erythemic skin. The combination of ingredients includes niacinamide, acetyl dipeptide-1 cetyl ester, palmitoyl oligopeptide, and palmitoyl tetrapeptide-7. The niacinamide can inhibit skin pigmentation. Both of palmitoyl oligopeptide and palmitoyl tetrapeptide-7 can increase the production of collagen in skin, thereby filling in fine lines and wrinkles Acetyl dipeptide-1 cetyl ester can treat inflamed or erythemic skin by inhibiting TNF-α and Il-1-α in skin. This combination of ingredients can be used in any of the compositions disclosed throughout the specification (e.g., moisturizes, cleansers, eye creams, or aqueous gels), thereby providing the aforementioned attributes to the compositions. In a particularly preferred embodiment, the combination of ingredients is used in the aqueous gel composition disclosed throughout the specification. The amounts of the ingredients to be included in a composition of the present invention can be modified as desired to achieve a particular result. In a preferred embodiment, the amounts can include 1% to 3% w/w niacinamide, 0.001% to 0.1% w/w acetyl dipeptide-1 cetyl ester, 0.00001% to 0.001% w/w palmitoyl oligopeptide, and 0.00001% to 0.001% w/w palmitoyl tetrapeptide-7.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Also disclosed in the context of the present invention are embodiments 1 to 40. Embodiment 1 is a topical skin composition comprising: water; glycerin; butylene glycol; ethylene/acrylic acid copolymer; *Butyrospermum parkii* butter; disodium EDTA; and triethanolamine. Embodiment 2 is the topical skin composition of embodiment 1, comprising 25% to 70% w/w of water; 1% to 10% w/w of glycerin; 0.5% to 6% w/w of butylene glycol; 0.5% to 3% w/w of ethylene/acrylic acid copolymer; 0.5% to 5% w/w of *Butyrospermum parkii* butter; 0.01% to 0.2% w/w of disodium EDTA; and 0.05% to 1% w/w of triethanolamine. Embodiment 3 is the topical skin composition of any of embodiments 1-2, wherein it is capable of moisturizing skin. Embodiment 4 is the topical skin composition of any of embodiments 1-3, wherein the composition is formulated as a cream and has a sun protection factor of around 30. Embodiment 5 is the topical skin composition of any of embodiments 1-4, further comprising: oxybenzone; octisalate; octocrylene; homosalate; avobenzone; and styrene/acrylates copolymer. Embodiment 6 is the topical skin composition of embodiment 5, comprising 3.0% to 5.0% w/w of oxybenzone; 4.0% to 5.0% w/w of octisalate; 2.0% to 3.0% w/w of octocrylene; 5.0% to 7.0% w/w of homosalate; 1.0% to 3.0% w/w of avobenzone; and 1.0% to 7.0% w/w of styrene/acrylates copolymer. Embodiment 7 is the topical skin composition of any of embodiments 5-6, further comprising: glycereth-26; allantoin; xantham gum; panthenol; tocopherol acetate; sodium PCA; benzyl alcohol; PEG-100 stearate; lauramine oxide; C9-15 alkyl phosphate; polymethylsilsesquioxane; methyl trimethicone; and acrylates/dimethicone copolymer. Embodiment 8 is the topical skin composition of any of embodiments 5-6, further comprising: trisiloxane; cetearyl alcohol; C12-15 alkyl benzoate; phenethyl benzoate; polyester-7; ceteth-20 phosphate; neopentyl glycol diheptanoate; dimethicone; dipropylene glycol dibenzoate; dicetyl phosphate; caprylyl glycol; methyl trimethicone; methyldihydrojasmonate; hydroxyethyl acrylate/sodium acryloyldimethyl taurate copolymer; pentylene glycol; squalane; ethylene brassylate; ethyl linalool; PPG-15 stearyl ether benzoate; sorbic acid; polysorbate 60; isobutyl methyl tetrahydropyranol; trimethylbenzenepropanol; sorbitan isostearate; phenylisohexanol; and ammonium hydroxide. Embodiment 9 is the topical skin composition of any of embodiments 5-6, further comprising: trisiloxane; C12-15 alkyl benzoate; phenethyl benzoate; polyester-7; neopentyl glycol diheptanoate; glyceryl stearate; hydroxyethyl acrylate/sodium acryloyldimethyl taurate copolymer; dipropylene glycol dibenzoate; arachidyl alcohol; caprylyl glycol; squalane; methyldihydrojasmonate; potassium cetyl phosphate; dimethicone; steareth-21; hydrogenated palm glycerides; pentylene glycol; behenyl alcohol; arachidyl glucoside; ethylene brassylate; PPG-15 stearyl ether benzoate; ethyl linalool; polysorbate 60; hydrogenated lecithin; sorbic acid; isobutyl methyl tetrahydropyranol; trimethylbenzenepropanol; sorbitan isostearate; phenylisohexanol; and ammonium hydroxide. Embodiment 10 is the topical skin composition of any of embodiments 5-6, further comprising: trisiloxane; C12-15 alkyl benzoate; phenethyl benzoate; polyester-7; neopentyl glycol diheptanoate; glyceryl stearate; hydroxyethyl acrylate/sodium acryloyldimethyl taurate copolymer; dipropylene glycol dibenzoate; arachidyl alcohol; caprylyl glycol; squalane; methyldihydrojasmonate; potassium cetyl phosphate; dimethicone; hydrogenated palm glycerides; pentylene glycol; behenyl alcohol; arachidyl glucoside; ethylene brassylate; ethyl linalool; PPG-15 stearyl ether benzoate; polysorbate 60; hydrogenated lecithin; sorbic acid; isobutyl methyl tetrahydropyranol; trimethylbenzenepropanol; sorbitan isostearate; phenylisohexanol; and ammonium hydroxide. Embodiment 11 is the topical skin composition of any of embodiments 5-6, further comprising: C12-15 alkyl benzoate; trisiloxane; polyester-7; neopentyl glycol diheptanoate; glyceryl stearate; benzyl alcohol; hydroxyethyl acrylate/sodium acryloydimethyl taurate copolymer; arachidyl alcohol; caprylyl glycol; squalane; methyldihydrojasmonate; potassium cetyl phosphate; dimethicone; hydrogenated palm glycerides; pentylene glycol; behenyl alcohol; arachidyl glucoside; ethylene brassylate; ethyl linalool; polysorbate 60; C9-15 alkyl phosphate; tocopheryl acetate; hydrogenated lecithin; sorbic acid; isobutyl methyl tetrahydropyranol; trimethylbenzenepropanol; sorbitan isostearate; phenylisohexanol; and ammonium hydroxide. Embodiment 12 is the topical skin composition of any of embodiments 5-6, further comprising: trisiloxane; C12-15 alkyl benzoate; phenethyl benzoate; polyester-7; neopentyl glycol diheptanoate; glyceryl stearate; dimethicone; hydroxyethyl acrylate/sodium acryloydimethyl taurate copolymer; phenoxyethanol; dipropylene glycol dibenzoate; ceteryl alcohol; caprylyl glycol; squalane; methyldihydrojasmonate; ceteth-20 phosphate; pentylene glycol; dicetyl phosphate; ethylene brassylate; ethyl linalool; PPG-15 stearyl ether benzoate; polysorbate 60; sorbic acid; isobutyl methyl tetrahydropyranol; trimethylbenzenepropanol; sorbitan isostearate; phenylisohexanol; and ammonium hydroxide. Embodiment 13 is the topical skin composition of embodiment 7, further comprising: trisiloxane; C12-15 alkyl benzoate; butyloctyl salicylate; glyceryl stearate; trimethypentanediol/adipic acid/glycerin crosspolymer; hydroxyethyl acrylate/sodium acryloyldimethyl taurate copolymer; dipropylene glycol dibenzoate; arachidyl alcohol; caprylyl glycol; squalane; methyldihydrojasmonate; potassium cetyl phosphate; dimethicone; steareth-21; hydrogenated palm glycerides; pentylene glycol; behenyl alcohol; arachidyl glucoside; ethylene brassylate; ethyl linalool; PPG-15 stearyl ether benzoate; polysorbate 60; hydrogenated lecithin; sorbic acid; isobutyl methyl tetrahydropryranol; trimethylbenzenepropanol; adenosine; sorbitan isostearate; phenylisohexanol; ammonium hydroxide; and sodium benzoate. Embodiment 14 is the topical skin composition of embodiment 13, further comprising *Opuntia tuna* fruit extract. Embodiment 15 is the topical skin composition of embodiment 14, comprising 0.0001% to 0.1% w/w of *Opuntia tuna* fruit extract. Embodiment 16 is a method of protecting skin from UV radiation comprising topically applying any one of the compositions of embodiments 1-15 to skin in need thereof, wherein topical application of said compositions protects the skin from UV radiation. Embodiment 17 is the topical skin composition of any of embodiments 1-2, wherein it is capable of treating the skin around the eyes. Embodiment 18 is the topical skin composition of any of claim 1, 2, or 17, wherein the composition is formulated as a cream capable of reducing the appearance of dark circles or puffy eyes. Embodiment 19 is the topical skin composition of embodiment 1, further comprising: phenoxyethanol; Carbopol Ultrez 10; cetearyl glucoside; chlorphenesin; adenosine; betaine; Hispagel 200 NS; cetearyl alcohol; ceteareth-20; C12-15 alcohols benzoate; hydrogenated polydecene; polyethylene; cetyl esters; behenyl alcohol; eldew PS-304; dipalmit hydroxyproline; dimethicone silicone; Glycacil 2000; and palmitoyl tetrapeptide-7. Embodiment 20 is the topical skin composition of any one of embodiments 1-2, comprising 0.5% to 1.5% w/w of phenoxyethanol; 0.2% to 0.4% w/w of Carbopol Ultrez 10; 0.5% to 1.5% w/w of cetearyl glucoside; 0.2% to 0.3% w/w of chlorphenesin; 0.01% to 0.1% w/w of adenosine; 1.0% to 5.0% w/w of betaine; 2.0% to 3.0% w/w of Hispagel 200 NS; 0.25% to 1.5% w/w of cetearyl alcohol; 0.25% to 1.5% w/w of ceteareth-20; 2.0% to 4.0% w/w of C12-15 alcohols benzoate; 2.0% to 3.0% w/w of hydrogenated polydecene; 2.0% to 3.0% w/w of polyethylene; 1.0% to 1.5% w/w of cetyl esters; 1.0% to 1.5% w/w of behenyl alcohol; 0.25% to 1.0% w/w of eldew PS-304; 0.25% to 1.0% w/w of dipalmit hydroxyproline; 0.5% to 1.5% w/w of dimethicone silicone; 0.1% to 0.2% w/w of Glycacil 2000; and 1.0% to 3.0% w/w of palmitoyl tetrapeptide-7. Embodiment 21 is the topical skin composition of embodiment 19, further comprising *Opuntia tuna* fruit extract. Embodiment 22 is the topical skin composition of embodiment 21, comprising 0.01% to 0.1% w/w of *Opuntia tuna* fruit extract. Embodiment 23 is a method of reducing the appearance of dark circles or puffiness in the periorbital region of a person's face comprising topically applying any one of the compositions of embodiments 1, 2, or 18-22 to skin in need thereof, wherein topical application reduces the appearance of dark circles or puffiness in the periorbital region of a person's face. Embodiment 24 is a topical skin composition comprising: water; glycerin; triethanolamine; phenoxyethanol; disodium EDTA; hydroxypropyl cyclodextrin; and iodopropynyl butylcarbamate. Embodiment 25 is the topical skin composition of embodiment 24, comprising 70% to 95% w/w of water; 1% to 10% w/w glycerin; 0.1% to 2% w/w triethanolamine; 0.1% to 2% w/w phenoxyethanol; 0.01% to 0.2% w/w disodium EDTA; 0.01% to 0.2% w/w hydroxypropyl cyclodextrin; and 0.001% to 0.02% w/w iodopropynyl butylcarbamate. Embodiment 26 is the topical skin composition of embodiment 25, wherein the composition is a skin cleanser. Embodiment 27 is the topical skin composition of embodiment 26 further comprising: tea-lauryl sulfate; cocamidopropyl betaine; propylene glycol; sodium methyl cocoyl taurate; dimethicone; lauramine oxide; and acrylates/C10-30 alkyl acrylate crosspolymer. Embodiment 28 is the topical skin composition of embodiment 27, comprising 5% to 10% w/w tea-lauryl sulfate; 1% to 3% w/w cocamidopropyl betaine; 1% to 3% w/w propylene glycol; 1% to 3% w/w sodium methyl cocoyl taurate; 1% to 3% w/w dimethicone; 0.1% to 3% w/w lauramine oxide; and 0.1% to 3% w/w acrylates/C10-30 alkyl acrylate crosspolymer. Embodiment 29 is the topical skin composition of embodiment 28 further comprising: sodium chloride; caprylyl glycol; C12-15 alkyl benzoate; benzyl alcohol; PEG-150 distearate; PPG-26-buteth-26; and PEG-40 hydrogenated castor oil. Embodiment 30 is the topical skin composition of embodiment 29, comprising 0.1% to 1% w/w sodium chloride; 0.1% to 1% w/w caprylyl glycol; 0.1% to 1% w/w C12-15 alkyl benzoate; 0.1% to 1% w/w benzyl alcohol; 0.1% to 1% w/w PEG-150 distearate; 0.1% to 1% w/w PPG-26-buteth-26; and 0.1% to 1% w/w PEG-40 hydrogenated castor oil. Embodiment 31 is the topical skin composition of embodiment 25, wherein the composition is an aqueous gel that is capable of moisturizing skin, treating fine lines and wrinkles, reducing skin pigmentation, or treating erythemic or inflamed skin. Embodiment 32 is the topical skin composition of embodiment 31, further comprising: niacinamide; acetyl dipeptide-1 cetyl ester; palmitoyl oligopeptide; and palmitoyl tetrapeptide-7. Embodiment 33 is the topical skin composition of embodiment 32, comprising: 1% to 3% w/w niacinamide; 0.001% to 0.1% w/w acetyl dipeptide-1 cetyl ester; 0.00001% to 0.001% w/w palmitoyl oligopeptide; and 0.00001% to 0.001% w/w palmitoyl tetrapeptide-7. Embodiment 34 is the topical skin composition of embodiment 33 further comprising: butylene glycol; hydroxypropyl cyclodextrin; and adenosine. Embodiment 35 is the topical skin composition of embodiment 34, comprising: 5% to 10% w/w butylene glycol; 0.01% to 0.3% w/w hydroxypropyl cyclodextrin; and 0.01% to 0.3% w/w adenosine. Embodiment 36 is the topical skin composition of embodiment 35 further comprising: acrylates/vinyl isodecanoate crosspolymer; and hydroxyethylcellulose. Embodiment 37 is the topical skin composition of embodiment 36, comprising 0.1% to 3% w/w acrylates/vinyl isodecanoate crosspolymer; and 0.1% to 3% w/w hydroxyethylcellulose. Embodiment 38 is a method of cleansing skin comprising applying to skin a composition of any of embodiments 24-30. Embodiment 39 is a method of moisturizing skin, treating fine lines and wrinkles, reducing skin pigmentation, or treating erythemic or inflamed skin comprising applying to skin in need thereof any one of the compositions of embodiments 31 to 37. Embodiment 40 is the method of embodiment 39 wherein the composition is applied to facial skin.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or over night or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse of composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the compositions' abilities to moisturize skin, reduce the appearance of fine lines and wrinkles, inhibit skin pigmentation, and/or treat inflamed or erythemic skin.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Given the number of various products on the market today, a person is oftentimes at a loss to identify an appropriate product. In addition, the skin of men has different needs from the skin of women and, while women have a large selection of skincare products to choose from, the options available formulated specifically for men are much fewer. This leaves them with the choice of having to identify one of a large number of female-designed products or of selecting from a narrower range of products designed for male skin. With this backdrop in mind, the inventors discovered various formulations that can be used to treat and protect skin, and in particular men's skin. These formulations can be used individually or in a regimen-based format.

The cosmetic moisturizers of the present invention can be used to moisturize, maintain, and improve the health of skin. For instance, the moisturizers can provide many advantages including: moisturizing skin; maintaining skin hydration; nourishing skin; controlling excess sebum or oil build-up; leaving the skin feeling non-greasy or non-oily; protecting the skin from damaging rays of the sun. They are typically formulated as oil-in-water emulsions.

One cream of the present invention is designed to be used during the day due, in part, to its sun protection factor (SPF) 30 protection for skin. It can include one, a combination of, or all of oxybenzone, octisalate, octocrylene, homosalate, avobenzone, styrene/acrylates copolymer, water, glycerin, butylene glycol, ethylene/acrylic acid copolymer, *Butyrospermum parkii* butter, disodium EDTA, triethanolamine, glycereth-26, allantoin, xantham gum, panthenol, tocopherol acetate, sodium PCA, benzyl alcohol, PEG-100 stearate, lauramine oxide, C9-15 alkyl phosphate, polymethylsilsesquioxane, methyl trimethicone, acrylates/dimethicone copolymer, trisiloxane, cetearyl alcohol, C12-15 alkyl benzoate, phenethyl benzoate, polyester-7, ceteth-20 phosphate, neopentyl glycol diheptanoate, dimethicone, dipropylene glycol dibenzoate, dicetyl phosphate, caprylyl glycol, methyl trimethicone, methyldihydrojasmonate, hydroxyethyl acrylate/sodium acryloyldimethyl taurate copolymer, pentylene glycol, squalane, ethylene brassylate, ethyl linalool, PPG-15 stearyl ether benzoate, sorbic acid, polysorbate 60, isobutyl methyl tetrahydropyranol, trimethylbenzenepropanol, sorbitan isostearate, phenylisohexanol, ammonium hydroxide, glyceryl stearate, arachidyl alcohol, potassium cetyl phosphate, steareth-21, hydrogenated palm glycerides, behenyl alcohol, arachidyl glucoside, hydrogenated lecithin, benzyl alcohol, hydroxyethyl acrylate/sodium acryloydimethyl taurate copolymer, C9-15 alkyl phosphate, tocopheryl acetate, phenoxyethanol, ceteryl alcohol, trimethypentanediol/adipic acid/glycerin crosspolymer, isobutyl methyl tetrahydropryranol, adenosine, sodium benzoate, and *Opuntia tuna* fruit extract. Further, additional ingredients can be added to obtain a desired tactile property and/or to obtain a particular skin benefit.

In a further instance, there is disclosed a cream that is designed for skin around the eyes (periorbital region). The cream can be designed in such a manner so as to account for the thinner and more sensitive skin in the periorbital region of a person's face. The formulation may minimize the appearance of under-eye bags and dark circles. The formulation can include one of, any combination of, or all of water, glycerin, butylene glycol, ethylene/acrylic acid copolymer, *Butyrospermum parkii* butter, disodium EDTA, triethanolamine, phenoxyethanol, Carbopol Ultrez 10, cetearyl glucoside, chlorphenesin, adenosine, betaine, Hispagel 200 NS, cetearyl alcohol, ceteareth-20, C12-15 alcohols benzoate, hydrogenated polydecene, polyethylene, cetyl esters, behenyl alcohol, eldew PS-304, dipalmit hydroxyproline, dimethicone silicone, Glycacil 2000, palmitoyl tetrapeptide-7, and *Opuntia tuna* fruit extract. Further, additional ingredients can be added to obtain a desired tactile property and/or to obtain a particular skin benefit.

In another instance, there is a disclosed a cleanser. The formulation can include one, a combination of, or all of water, glycerin, triethanolamine, phenoxyethanol, disodium EDTA, hydroxypropyl cyclodextrin, iodopropynyl butylcarbamate, tea-lauryl sulfate, cocamidopropyl betaine, propylene glycol, sodium methyl cocoyl taurate, dimethicone, lauramine oxide, acrylates/C10-30 alkyl acrylate crosspolymer, sodium chloride, caprylyl glycol, C12-15 alkyl benzoate, benzyl alcohol, PEG-150 distearate, PPG-26-buteth-26, and PEG-40 hydrogenated castor oil. Further, additional ingredients can be added to obtain a desired tactile property and/or to obtain a particular skin benefit.

Also, herein there is disclosed an aqueous gel that is capable of moisturizing skin. The formulation can include one, a combination of, or all of water, glycerin, triethanolamine, phenoxyethanol, disodium EDTA, hydroxypropyl cyclodextrin, iodopropynyl butylcarbamate, butylene glycol, niacinamide, hydroxypropyl cyclodextrin, adenosine, acetyl dipeptide-1 cetyl ester, palmitoyl oligopeptide, palmitoyl tetrapeptide-7, acrylates/vinyl isodecanoate crosspolymer, and hydroxyethylcellulose. Further, additional ingredients can be added to obtain a desired tactile property and/or to obtain a particular skin benefit.

A. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

B. Vehicles

The compositions of the present invention can be incorporated into all types of vehicles. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

C. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea officinalis extract, apricot (*prunus armeniaca*) kernel oil, arginine, arginine aspartate, arnica montana extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, macadamia ternifolia nut oil, maltitol, matricaria (*chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquarternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

D. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Formulations

The formulations in Tables 1 and 2 are each moisturizers, the formulations in Tables 3 and 4 are each eye treatment formulations, the formulation in Table 5 is a cleanser, and the formulation in Table 6 is an aqueous gel-based serum capable of moisturizing the skin.

TABLE 1*

| Ingredient | % Concentration (by weight) |
| --- | --- |
| Water | 39 to 46.5 |
| Oxybenzone | 4 |
| Octisalate | 4.5 |
| Octocrylene | 2 to 3 |
| Homosalate | 6 |
| Avobenzone | 2 |
| Styrene/acrylates copolymer | 1.7 .75 |
| Glycerin | 2.5 To 5 |
| Butylene glycol | 1 to 3 |
| Ethylene/acrylic acid copolymer | 0.5 |
| Butyrospermum parkii butter | 0.5 |
| Disodium EDTA | 0.23 |
| Triethanolamine | 0.05 to 0.55 |
| Glycereth-26 | 4 |
| Allantoin | 0.08 |
| Xantham gum | 0.25 |
| Panthenol | 0.1 |
| Tocopherol acetate | 0.1 |
| Sodium PCA | 0.05 to 0.1 |
| Benzyl alcohol | 0.9 |
| PEG-100 stearate | 0.7 to 0.8 |
| Lauramine oxide | 0.2 to 0.9 |
| C9-15 alkyl phosphate | 0.11 |
| Polymethylsilsesquioxane | 1 |
| Methyl trimethicone | 0.6 |
| Acrylates/dimethicone copolymer | 0.4 |
| Excipients** | q.s. |

*Formulation can be prepared by mixing the ingredients in a beaker under heat 70-75° C. until homogenous. Subsequently, the formulation can be cooled to standing room temperature (20-25° C.).
**Excipients can be added, for example, to modify the rheological properties of the composition. Alternatively, the amount of water can be varied so long as the amount of water in the composition is at least 30% w/w, and preferably between 35 to 85% w/w.

TABLE 2*

| Ingredient | % Concentration (by weight) |
| --- | --- |
| Water | 43.5 |
| Homosalate | 6 |
| Octisalate | 4.5 |
| Oxybenzone | 4 |
| Octocrylene | 3 |
| Avobenzone | 2 |
| Styrene/acrylates copolymer | 1.7 |
| Glycerin | 5 |
| Glycereth-26 | 4 |
| Butylene Glycol | 3 |
| Trisiloxane | 2.5 |
| C12-15 alkyl benzoate | 2.1 |
| Butyloctyl salicylate | 2 |
| Glyceryl stearate | 1 |
| Benzyl alcohol | 0.9 |
| Phenoxyethanol | 0.8 |
| Arachidyl alcohol | 0.6 |
| Caprylyl glycol | 0.6 |
| Dimethicone | 0.5 |
| Ethylene/acrylic acid copolymer | 0.5 |
| Butyrospermum parkii | 0.5 |
| Disodium EDTA | 0.2 |
| Triethanolamine | 0.08 |

TABLE 2*-continued

| Ingredient | % Concentration (by weight) |
| --- | --- |
| Optunia tuna fruit extract | 0.0005 |
| Excipients | q.s. |

*Formulation can be prepared by mixing the ingredients in a beaker under heat 70-75° C. until homogenous. Subsequently, the formulation can be cooled to standing room temperature (20-25° C.).
**Excipients can be added, for example, to modify the rheological properties of the composition. Alternatively, the amount of water can be varied so long as the amount of water in the composition is at least 35% w/w, and preferably between 40 to 85% w/w.?

TABLE 3*

| Ingredient | % Concentration (by weight) |
| --- | --- |
| Water | 62 |
| Glycerin | 1.5 |
| Butylene Glycol | 5 |
| Betaine | 4 |
| Triethanolamine | 0.5 |
| Dimethicone | 1 |
| Disodium EDTA | 0.05 |
| Phenoxyethanol | 0.9 |
| Butyrospermum parkii | 4 |
| Ethylene/acrylic acid copolymer | 2 |
| Palmitoyl tetrapeptide-7 | 2 |
| Hydrogenated polydecene | 2.25 |
| Polyethylene | 2.25 |
| Cetyl esters | 1.25 |
| Behenyl alcohol | 1.25 |
| C12-15 alcohols benzoate | 2 |
| Excipients** | q.s. |

*Formulation can be prepared by mixing the ingredients in a beaker under heat 70-75° C. until homogenous. Subsequently, the formulation can be cooled to standing room temperature (20-25° C.).
**Excipients can be added, for example, to modify the rheological properties of the composition. Alternatively, the amount of water can be varied so long as the amount of water in the composition is at least 60% w/w, and preferably between 60 to 85% w/w.

TABLE 4*

| Ingredient | % Concentration (by weight) |
| --- | --- |
| Water | 62 |
| Glycerin | 1.5 |
| Butylene Glycol | 5 |
| Betaine | 4 |
| Triethanolamine | 0.5 |
| Dimethicone | 1 |
| Disodium EDTA | 0.05 |
| Phenoxyethanol | 0.9 |
| Butyrospermum parkii | 4 |
| Ethylene/acrylic acid copolymer | 2 |
| Palmitoyl tetrapeptide-7 | 2 |
| Hydrogenated polydecene | 2.25 |
| Polyethylene | 2.25 |
| Cetyl esters | 1.25 |
| Behenyl alcohol | 1.25 |
| C12-15 alcohols benzoate | 2 |
| Optunia tuna fruit extract | 0.05 |
| Excipients** | q.s. |

*Formulation can be prepared by mixing the ingredients in a beaker under heat 70-75° C. until homogenous. Subsequently, the formulation can be cooled to standing room temperature (20-25° C.).
**Excipients can be added, for example, to modify the rheological properties of the composition. Alternatively, the amount of water can be varied so long as the amount of water in the composition is at least 60% w/w, and preferably between 60 to 85% w/w.

TABLE 5*

| Ingredient | % Concentration (by weight) |
| --- | --- |
| water | 75 |
| glycerin | 3 |

TABLE 5*-continued

| Ingredient | % Concentration (by weight) |
|---|---|
| triethanolamine | 0.8 |
| phenoxyethanol | 0.7 |
| disodium EDTA | 0.1 |
| hydroxypropyl cyclodextrin | 0.07 |
| iodopropynyl butylcarbamate | 0.009 |
| tea-lauryl sulfate | 8 |
| cocamidopropyl betaine | 2.4 |
| propylene glycol | 2 |
| sodium methyl cocoyl taurate | 1.5 |
| dimethicone | 1 |
| lauramine oxide | 0.9 |
| acrylates/C10-30 alkyl acrylate crosspolymer | 0.75 |
| sodium chloride | 0.7 |
| caprylyl glycol | 0.6 |
| C12-15 alkyl benzoate | 0.5 |
| benzyl alcohol | 0.5 |
| PEG-150 distearate | 0.5 |
| PPG-26-buteth-26 | 0.3 |
| PEG-40 hydrogenated castor oil | 0.2 |
| Excipients** | q.s. |

*Formulation can be prepared by mixing the ingredients in a beaker under heat 70-75° C. until homogenous.
**Excipients can be added, for example, to modify the rheological properties of the composition. Alternatively, the amount of water can be varied so long as the amount of water in the composition is at least 60% w/w, and preferably between 60 to 85% w/w.

TABLE 6*

| Ingredient | % Concentration (by weight) |
|---|---|
| water | 88 |
| glycerin | 1.6 |
| triethanolamine | 0.25 |
| phenoxyethanol | 0.9 |
| disodium EDTA | 0.1 |
| hydroxypropyl cyclodextrin | 0.07 |
| iodopropynyl butylcarbamate | 0.009 |
| butylene glycol | 6.3 |
| niacinamide | 2 |
| hydroxypropyl cyclodextrin | 0.07 |
| adenosine | 0.04 |
| acetyl dipeptide-1 cetyl ester | 0.01 |
| palmitoyl oligopeptide | 0.0003 |
| palmitoyl tetrapeptide-7 | 0.0001 |
| acrylates/vinyl isodecanoate crosspolymer | 0.25 |
| hydroxyethylcellulose | 0.22 |
| Excipients** | q.s. |

*Formulation can be prepared by mixing the ingredients in a beaker under heat 70-75° C. until homogenous.
**Excipients can be added, for example, to modify the rheological properties of the composition. Alternatively, the amount of water can be varied so long as the amount of water in the composition is at least 60% w/w, and preferably between 60 to 95% w/w.

A formulation having the characteristics of the Table 1 formulation, the Table 2 formulation, the Table 5 formulation, or the Table 6 formulation can be used in a regimen that also includes an eye care formulation. A formulation having the characteristics of the Table 3 formulation, the Table 4 formulation, the Table 5 formulation, or the Table 6 formulation can be used in a regimen that also includes a moisturizer or moisturizing sunscreen formulation. A formulation having the characteristics of the Table 1 formulation, the Table 2 formulation, the Table 3 formulation, the Table 4 formulation, or the Table 6 formulation formulations can be used in a regiment that also includes a skin cleanser. A formulation having the characteristics of the Table 1 formulation, the Table 2 formulation, the Table 3 formulation, the Table 4 formulation, or the Table 5 formulation can be used in a regimen that also includes a serum that is capable of moisturizing the skin.

The ingredients niacinamide, acetyl dipeptide-1 cetyl ester, palmitoyl oligopeptide, and palmitoyl tetrapeptide-7 were individually tested and found to have beneficial properties for skin. The data for these ingredients are summarized in Table 7.

TABLE 7

| Ingredient | Data |
|---|---|
| Acetyl dipeptide-1 Cetyl Ester (suppied by Sederma under the tradename Calmosensine) | Inhibit IL-1α & TNF-α Production by Human Epidermal Keratinocytes (IL-1α-97% inhibition) (TNF-α-88%) |
| Palmitoyl oligopeptide with palmitoyl tetrapeptide-7 (supplied by Sederma under the tradename Matrixyl 3000) | Stimulates collagen synthesis by fibroblasts cultures. |
| Niacinamide | Inhibits Melanogenesis with Mouse Melanocytes (B16-F1 Assay) (−28%) |

Tumor Necrosis Factor Alpha (TNF-α) Assay:

The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color develops in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EpiLife standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

B16 Pigmentation Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion was measured by absorbance at 405 nm and cellular viability was quantified.

IL-1α Assay:

A quantitative sandwich enzyme immunoassay technique (ELISA) was used to measure IL-1α in cell culture supernates. A monoclonal antibody that is specific for IL-1α was pre-coated onto a microplate. Standards and treatment samples are then pipetted into the wells and any IL-1α present is bound by the immobilized antibody. After washing away any unbound substances, an enzyme-linked polyclonal antibody specific for IL-1α is added to the wells. Following a wash to remove any unbound antibody-enzyme reagent, a substrate solution is added to the wells and color develops in proportion to the amount of IL-1α bound which was secreted in response to the treatment.

Example 2

Assays

Additional assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Collagen Stimulation Assay:

Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured. Subconfluent normal human adult epidermal fibroblasts (Cascade Biologics) cultivated in standard DMEM growth medium with 10% fetal bovine serum (Mediatech) at 37° C. in 10% $CO_2$, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from Takara (#MK101).

Antioxidant (AO) Assay:

An in vitro bioassay that measures the total antioxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®•+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations. The assay relied on antioxidants in the sample to inhibit the oxidation of ABTS® (2,2'-azino-di-[3-ethylbenzthiazoline sulphonate]) to ABTS®•+ by metmyoglobin. The capacity of the antioxidants in the sample to prevent ABTS oxidation can be compared with that Trolox, a water-soluble tocopherol analogue, and was quantified as a molar Trolox equivalent.

ORAC Assay:

Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Matrix Metalloproteinase Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methylpentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\epsilon$=13,600 M-1 cm-1 at pH 6.0 and above 7). The active ingredients, any one of the combination of ingredients, or compositions having said combinations disclosed in the specification can be assayed.

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay:

An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and mixtures incubated for an additional 10 min at room temperature. Colorimetric substrate can be added to terminate catalysis and color progression was evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay:

EnzChek® Elastase Assay (Kit#E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, chloromethyl ketone, can be used as a selective, collective inhibitor of elastase when utilizing the EnzChek Elastase Assay Kit for screening for elastase inhibitors.

Oil Control Assay:

An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay:

In other non-limiting aspects, the efficacy of each of the active ingredients, any one of the combination of ingredients, or compositions having said combinations disclosed in the specification compositions can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A topical skin composition comprising: 70% to 95% w/w of water; 1% to 10% w/w glycerin; 0.1% to 2% w/w triethanolamine; 0.1% to 2% w/w phenoxyethanol; 0.01% to 0.2% w/w disodium EDTA; 0.01% to 0.3% w/w hydroxypropyl cyclodextrin; and 0.001% to 0.02% w/w iodopropynyl butylcarbamate.

2. The topical skin composition of claim 1, wherein the composition is a skin cleanser.

3. The topical skin composition of claim 2, further comprising:
TEA-lauryl sulfate; cocamidopropyl betaine; propylene glycol; sodium methyl cocoyl taurate; dimethicone; lauramine oxide; and acrylates/C10-30 alkyl acrylate crosspolymer.

4. The topical skin composition of claim 3, comprising 5% to 10% w/w TEA-lauryl sulfate; 1% to 3% w/w cocamidopropyl betaine; 1% to 3% w/w propylene glycol; 1% to 3% w/w sodium methyl cocoyl taurate; 1% to 3% w/w dimethicone; 0.1% to 3% w/w lauramine oxide; and 0.1% to 3% w/w acrylates/C10-30 alkyl acrylate crosspolymer.

5. The topical skin composition of claim 4, further comprising: sodium chloride;

caprylyl glycol; C12-15 alkyl benzoate; benzyl alcohol; PEG-150 distearate; PPG-26-buteth-26; and PEG-40 hydrogenated castor oil.

6. The topical skin composition of claim 5, comprising 0.1% to 1% w/w sodium chloride; 0.1% to 1% w/w caprylyl glycol; 0.1% to 1% w/w C12-15 alkyl benzoate; 0.1% to 1% w/w benzyl alcohol; 0.1% to 1% w/w PEG-150 distearate; 0.1% to 1% w/w PPG-26-buteth-26; and 0.1% to 1% w/w PEG-40 hydrogenated castor oil.

7. The topical skin composition of claim 1, wherein the composition is an aqueous gel that is capable of moisturizing skin, treating fine lines and wrinkles, reducing skin pigmentation, or treating erythemic or inflamed skin.

8. The topical skin composition of claim 7, further comprising: niacinamide; acetyl dipeptide-1 cetyl ester; palmitoyl oligopeptide; and palmitoyl tetrapeptide-7.

9. The topical skin composition of claim 8, comprising: 1% to 3% w/w niacinamide; 0.001% to 0.1% w/w acetyl dipeptide-1 cetyl ester; 0.00001% to 0.001% w/w palmitoyl oligopeptide; and 0.00001% to 0.001% w/w palmitoyl tetrapeptide-7.

10. The topical skin composition of claim 9, further comprising: butylene glycol; and adenosine.

11. The topical skin composition of claim 10, comprising: 5% to 10% w/w butylene glycol; and 0.01% to 0.3% w/w adenosine.

12. The topical skin composition of claim 11, further comprising: acrylates/vinyl isodecanoate crosspolymer; and hydroxyethylcellulose.

13. The topical skin composition of claim 12, comprising 0.1% to 3% w/w acrylates/vinyl isodecanoate crosspolymer; and 0.1% to 3% w/w hydroxyethylcellulose.

14. The topical skin composition of claim 1, further comprising: niacinamide; acetyl dipeptide-1 cetyl ester; palmitoyl oligopeptide; and palmitoyl tetrapeptide-7.

15. The topical skin composition of claim 1, further comprising an effective amount of niacinamide to inhibit skin pigmentation in skin of a subject.

16. The topical skin composition of claim 1, further comprising an effective amount of acetyl dipeptide-1 cetyl ester to reduce inflammation and/or redness in skin of a subject.

17. The topical skin composition of claim 1, further comprising an effective amount of palmitoyl oligopeptide and palmitoyl tetrapeptide-7 to reduce fine lines and/or wrinkles in skin of a subject.

18. The topical skin composition of claim 14, further comprising: an effective amount of niacinamide to inhibit skin pigmentation in skin of a subject; an effective amount of acetyl dipeptide-1 cetyl ester to reduce inflammation and/or redness in skin of the subject; and an effective amount of palmitoyl oligopeptide and palmitoyl tetrapeptide-7 to reduce fine lines and/or wrinkles in skin of the subject.

19. A method for inhibiting skin pigmentation, reducing inflammation, reducing redness, reducing a fine line, and/or reducing a wrinkle in skin of a subject, the method comprising applying a topical skin composition of claim 14 to the skin of the subject.

20. A method for inhibiting skin pigmentation, reducing inflammation and/or redness, and reducing a fine line and/or a wrinkle in skin of a subject, the method comprising applying a topical skin composition of claim 18 to the skin of the subject.

* * * * *

UNITED STATES PATENT AND TRADEMARK OFFICE
CERTIFICATE OF CORRECTION

PATENT NO. : 9,937,119 B2  
APPLICATION NO. : 14/527435  
DATED : April 10, 2018  
INVENTOR(S) : Ricky Mendoza et al.

Page 1 of 1

It is certified that error appears in the above-identified patent and that said Letters Patent is hereby corrected as shown below:

On the Title Page

Item (56), please replace "CN 1097193541" with --CN 1997193541-- therefore.

Signed and Sealed this  
Twelfth Day of February, 2019

Andrei Iancu  
*Director of the United States Patent and Trademark Office*